(12) United States Patent  (10) Patent No.: US 8,343,258 B2
Guan  (45) Date of Patent: Jan. 1, 2013

(54) APPARATUS AND METHOD FOR CONTROLLING CONSTANT MASS FLOW TO GAS CHROMATOGRAPHY COLUMN

(75) Inventor: Xiaosheng Guan, Beijing (CN)

(73) Assignee: Agilent Technologies, Inc., Santa Clara, CA (US)

( * ) Notice: Subject to any disclaimer, the term of this patent is extended or adjusted under 35 U.S.C. 154(b) by 371 days.

(21) Appl. No.: 12/749,682

(22) Filed: Mar. 30, 2010

(65) Prior Publication Data

US 2011/0239860 A1  Oct. 6, 2011

(51) Int. Cl.
*B01D 53/02* (2006.01)
(52) U.S. Cl. .................... 95/89; 96/102; 96/105; 95/22; 73/23.42
(58) Field of Classification Search .............. 96/101, 96/102, 105; 95/19, 22, 82, 89; 73/23.42
See application file for complete search history.

(56) References Cited

U.S. PATENT DOCUMENTS

| | | | |
|---|---|---|---|
| 4,994,096 A | | 2/1991 | Klein et al. |
| 5,108,466 A | * | 4/1992 | Klein et al. ......................... 95/1 |
| 5,163,979 A | * | 11/1992 | Patrick et al. ..................... 95/19 |
| 5,339,673 A | * | 8/1994 | Nakagawa et al. .......... 73/23.36 |
| 5,431,712 A | | 7/1995 | Henderson et al. |
| 5,467,635 A | * | 11/1995 | Nakagawa et al. .......... 73/23.35 |
| 5,476,000 A | * | 12/1995 | Henderson et al. .......... 73/23.27 |
| 5,524,084 A | * | 6/1996 | Wang et al. .................... 702/100 |
| 5,545,252 A | * | 8/1996 | Hinshaw et al. ................. 95/15 |
| 5,567,227 A | * | 10/1996 | Henderson ........................ 95/22 |
| 5,711,786 A | * | 1/1998 | Hinshaw .......................... 95/82 |
| 5,803,951 A | * | 9/1998 | Wada et al. ....................... 95/22 |
| 5,938,817 A | * | 8/1999 | Shibamoto et al. ............... 95/23 |
| 5,958,246 A | * | 9/1999 | Tipler et al. ................... 210/656 |
| 6,036,747 A | * | 3/2000 | Blumberg et al. ................ 95/82 |
| 6,682,699 B2 | | 1/2004 | Mustacich et al. |
| 7,559,227 B2 | * | 7/2009 | Thompson ................... 73/23.42 |

\* cited by examiner

*Primary Examiner* — Robert Clemente

(57) ABSTRACT

A device for providing a constant mass flow rate to a downstream column system of a gas chromatograph includes a small full scale mass flow controller that controls carrier gas to flow at a first mass flow rate and a flow resistance element, including an inlet port connected to a sample inlet, an outlet port connected to the downstream column system, and a pressure sensing port in fluid communication with the outlet port and the mass flow controller. A sample inlet pressure controller controls the sample inlet at a first pressure, and a pressure sensor measures a second pressure of the carrier gas at the pressure sensing port. A set point of the first pressure is determined as a function of the second pressure, flow resistance of the flow resistance element, and a second mass flow rate from the inlet port to the outlet port of the flow resistance element.

20 Claims, 3 Drawing Sheets

APPARATUS AND METHOD FOR CONTROLLING CONSTANT MASS FLOW TO GAS CHROMATOGRAPHY COLUMN

BACKGROUND

Gas chromatography (GC) is used to separate solutes or components of an analyte sample for measurement. Generally, a GC device includes a downstream column system, including one or more capillary columns for separating the solutes. The columns are typically made of metal, glass or quartz, for example, and coated on the inside with a thin-film coating or stationary phase. The GC process includes mixing the analyte sample with a carrier gas, such as hydrogen or helium, and introducing the sample/carrier gas mixture into the column(s) using a continuous flow. Various solutes within the sample react differently with the stationary phase, and thus move at different speeds through the column(s), resulting in separation of the solutes. The separated solutes may then be detected by various detectors or provided as input to a mass spectrometer (MS) device, for example. An implementation in which the GC device provides samples in gaseous form to an inlet of an MS device is a gas chromatography mass spectrometer (GC-MS).

Conventional GC devices may include an electronic pressure control (EPC) system, which automatically controls carrier gas flow based on pressure sensing, for reproducible sample mixture injections at an inlet of the column(s), enabling chromatographic separation along the column(s) and detection upon the sample exiting the downstream column system. In order to achieve high column resolution and detector sensitivity, as well as short analysis time, the constant mass flow rate through the downstream column system is controlled to be a constant value.

For example, in a calculated pressure programming method, an example of which is described by KLEIN et al., in U.S. Pat. No. 4,994,096 (Feb. 19, 1991), which is hereby incorporated by reference, the pressure at a column inlet is controlled dynamically according to its relation with column mass flow rate, column dimension (e.g., length and inner diameter) and a temperature program to which the column subjected, given a particular type of carrier gas. However, the calculated pressure programming method is difficult to implement when the precise dimensions of the downstream column are not known, the downstream column includes multiple segments that are independently or temperature programmed, and/or the downstream column has additional flow or pressure control points before the detector to effect advanced functions, such as midpoint concurrent backflush and multidimensional GC, also known as heart cutting.

In addition, the calculated pressure programming method is difficult to implement when the downstream column does not feature a well-defined round cross-section. For example, when the column is not a drawn fused silica capillary, but rather, is microfabricated on silicon or other substrate, it may feature rectangular, trapezoidal or other variant cross-sectional geometry, and/or may have a serpentine layout to maximize usage of a small chip area, which contribute to a sophisticated and generally unknown relation to permeability exhibited by the column. Likewise, the calculated pressure programming method is difficult to implement when the column is subject to thermal control that is not fully integrated into the GC device, so that the temperature program of the column is unknown and/or difficult to monitor. An example of an unknown and/or difficult to monitor temperature program is a low thermal mass (LTM) column module that directly heats the column without a conventional GC oven, an example of which is described by MUSTACICH, et al. in U.S. Pat. No. 6,682,699 (Jan. 27, 2004), which is hereby incorporated by reference.

BRIEF DESCRIPTION OF THE DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
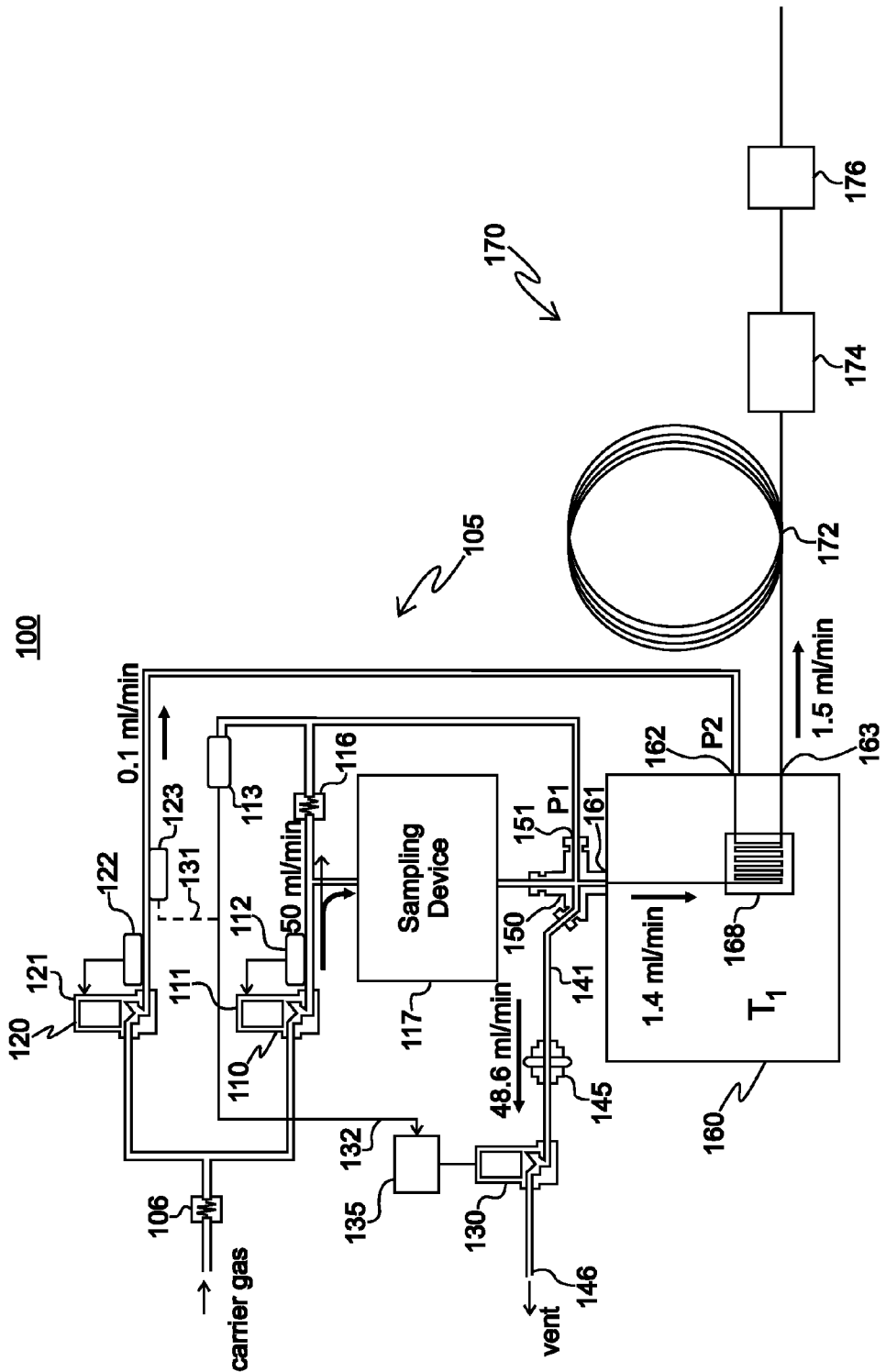
FIG. 1 is a block diagram illustrating a gas chromatography system including a constant mass flow rate control system, according to a representative embodiment.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

Generally, various representative embodiments provide a constant downstream column mass flow rate without needing to know detailed characteristics of the downstream column and operating environment, such as the geometry, dimensions, number of thermal zones and/or temperature programs of the downstream column, for example. Accordingly, as a practical matter, there is no need to know or calibrate the downstream column permeability for constant flow control and no need to know or monitor the downstream column temperature program for constant flow control. Also, the downstream column can be arbitrarily embodied in various different forms and geometry, and can be temperature programmed independently and differently from each other. In addition, the downstream column can be easily and efficiently set up for a constant mass flow rate through each column segment in midpoint backflush, heart cutting and other advanced configurations.

Further, in accordance with various representative embodiments, a device for providing a constant mass flow rate to a downstream column system of a gas chromatograph includes a small full scale mass flow controller, a flow resistance element, a sample inlet pressure controller and a pressure sensor. The small full scale mass flow controller is configured to control a carrier gas to flow at a first mass flow rate. The flow resistance element has a finite flow resistance, and includes an inlet port connected to a sample inlet, an outlet port connected to the downstream column system, and a pressure sensing port in fluid communication with both the outlet port and the small full scale mass flow controller for receiving the carrier gas at the first mass flow rate. The sample inlet pressure controller is configured to control the sample inlet at a first pressure. The pressure sensor is configured to measure a second pressure of the carrier gas at the pressure sensing port of the flow resistance element. A set point of the first pressure is determined as a function of the second pressure, the flow resistance of the flow resistance element, and a second mass flow rate from the inlet port to the outlet port of the flow resistance element, and the mass flow rate to the downstream column system is kept constant by controlling the first pressure to equal the first pressure set point.

FIG. 1 is a block diagram illustrating a gas chromatography system including a constant mass flow rate control system, according to a representative embodiment.

Referring to FIG. 1, GC system 100 has a gas sampling and inlet configuration that is operated in split mode, and includes flow rate control system 105 and downstream column system 170. The downstream column system 170 may be a complex setup of one or more downstream gas chromatography columns, each of which may have an unknown geometry, temperature program and/or flow resistance, for example. For purposes of discussion, the downstream column system 170 is shown as including LTM module 172, thermal modulator 174 and (one) capillary column, implemented by column chip 176. Of course, the downstream column system 170 may have various alternative configurations, including multiple columns having various implementations, without departing from the scope of present teachings.

Further, as stated above, the capillary column of the column chip 176 may have a flow path etched on a semiconductor substrate, for example. Therefore, the capillary column may have various cross-sectional shapes other than round, such as squares, rectangles, trapezoids, etc., and also may have a complex serpentine layout.

In various representative embodiments, non-pressure-programming constant mass flow rate control for the downstream column system 170 may be achieved, while various common inlet related functions are simultaneously performed, using a reconfigurable inlet pneumatic control, as described for example by HENDERSON et al., in U.S. Pat. No. 5,431,712 (Jul. 11, 1995), which is hereby incorporated by reference. It is understood that other non-reconfigurable inlet pneumatic control systems can also be similarly adapted to provide a non-pressure-programming constant mass flow rate control for any downstream column system.

The flow rate control system 105 has a first mass flow controller 110, which includes first proportional valve 111 and corresponding first flow sensor 112 for providing mass flow rate feedback. In an embodiment, the first mass flow controller 110 is a common or large full scale mass flow controller, e.g., having a full scale up to about 1000 sccm. The first mass flow controller 110 receives carrier gas from a carrier gas source (not shown), through optional flow resistant element 106, and controls the mass flow of the carrier gas to a predetermined first mass flow rate. In the depicted example, the first mass flow rate is 50 ml/min for purposes of discussion, although other first mass flow rates may be incorporated in various implementations.

The carrier gas output by the first mass flow controller 110 is divided into first and second portions. The first portion dominates the second portion for reasons explained below. The first portion of the carrier gas passes through a gas sampling device 117, which may include, but is not limited to, sample valve, purge and trap, headspace or thermal desorber, for the purpose of injecting a gas sample into a sample inlet, depicted as representative multi-port inlet 150, known as a Volatiles Interface (VI), which is commercially available, for example. The inlet 150 splits the sample/carrier gas mixture between split vent line 141 and the downstream column system 170 (via flow resistance element 160, discussed below).

The second portion of the carrier gas passes through a flow resistant element 116 to pressure port 151 of the inlet 150, where a first pressure $P_1$ at the inlet 150 is measured by first pressure sensor 113. The second portion of the carrier gas divided from the first portion is small, via operation of the flow resistance element 116, as compared to the first portion of the carrier gas. The second portion of the carrier gas prevents sample at the inlet 150 from diffusing back and fouling the first pressure sensor 113 for proper measurement of the first pressure $P_1$. Because the second portion is small, a negligible pressure drop is provided between the first pressure sensor 113 and the inlet 150, so that measurement of the first pressure $P_1$ is sufficiently accurate.

The flow rate control system 105 also has a second mass flow controller 120, which includes second proportional valve 121 and corresponding second flow sensor 122 for providing mass flow rate feedback. In an embodiment, the second mass flow controller 120 may be a small full scale mass flow controller, e.g., having a full scale of less than about 100 sccm. Unlike the first mass flow controller 110, the second mass flow controller 120 is thus able to control a small flow rate to the desired precision, typical for a capillary column of a GC device, such as representative LTM column module 172 and column chip 176 of the downstream column system 170. The second mass flow controller 120 receives carrier gas from the carrier gas source (not shown) through the optional flow resistant element 106. The second mass flow controller 120 controls the mass flow of the carrier gas to a predetermined second (small) mass flow rate. In the depicted example, the second mass flow rate is 0.1 ml/min for purposes of discussion, although other second mass flow rates may be incorporated in various implementations.

In addition, the flow rate control system 105 includes flow resistance element 160, which may be implemented by a pre-column chip, for example. The flow resistance element 160 has at least three ports, including inlet or pressure control port 161 connected to the inlet 150, pressure sensing port 162 connected to the second mass flow controller 120 and a second pressure sensor 123, and outlet port 163 connected to the downstream column system 170. The pressure sensing port 162 is thus in fluid communication with both the outlet port 163 and the second mass flow controller 120 for receiving the carrier gas at the second mass flow rate. A second pressure $P_2$ of the carrier gas at the pressure sensing port 162 is measured by the second pressure sensor 123.

The flow resistance element 160 further includes resistance portion 168, which provides a finite flow resistance R between the pressure control port 161 and the pressure sensing port 162. The flow resistance R has a known (e.g., previously determined) relationship for relating the mass flow rate through the flow resistance element 160 with the pressure differential between the pressure control port 161 and the pressure sensing port 162, at a constant temperature $T_1$ (or in accordance with a temperature program), based on the type of carrier gas. In various embodiments, the flow resistance R has a constant or fixed value at the temperature $T_1$. The value of the flow resistance R may be determined and calibrated prior to operation, and the relationship may be theoretically derived, empirically characterized or experimentally calibrated, for example, without departing from the scope of the present teachings. In the depicted example, the flow resistance mass flow rate (and thus corresponding flow resistance R) of the representative flow resistance element 160 is 1.4 ml/min for purposes of discussion, although other flow resistance mass flow rates and corresponding flow resistances may be incorporated in various implementations, as would be apparent to one having ordinary skill in the art.

The flow resistance element 160 outputs a constant downstream mass flow rate from the outlet port 163, which is the sum of the flow resistance mass flow rate through the resistance portion 168 and the second mass flow rate from the second mass flow controller 120. Thus, in the depicted example, the downstream mass flow rate is 1.5 ml/min, based on the illustrative flow resistance mass flow rate of 1.4 ml/min and second mass flow rate of 0.1 ml/min.

The resistance portion 168 may be a segment of capillary column, or a flow path fabricated in a closed substrate, such as a silicon chip or a metal plate, for example. The flow resistance element 160 may be hosted by a gas chromatography oven (not shown), or may be thermally controlled separately by a heated box (not shown), for example, to maintain the temperature $T_1$. In various embodiments, the heated box can be isothermal or temperature programmed.

As stated above, the inlet 150 enables splitting of the sample/carrier gas mixture between the split vent line 141 and the flow resistance element 160. In an embodiment, the split vent line 141 includes third proportional valve 130 and an optional vent trap 145, which absorbs sample volatiles so that only carrier gas is vented through the vent 146. In the depicted example, the vented mass flow rate is 48.6 ml/min for purposes of discussion, which is the difference between the first mass flow rate (e.g., 50 ml/min) and the flow resistance mass flow rate (e.g., 1.4 ml/min) although other first mass flow rates and flow resistance mass flow rates may be incorporated in various implementations.

As described in U.S. Pat. No. 5,431,712, for example, the inlet 150 performs the split mode injection via a so-called backpressure control scheme, implemented by the third proportional valve 130, the pressure sensor 113 and a feedback loop 132. More specifically, control of the first pressure $P_1$ at the back or upstream side of the third proportional valve 130 is achieved by constantly measuring the actual pressure at the inlet 150 using the pressure sensor 113 against a set point and regulating gas out of the third proportional valve 130, according to a control strategy, such as conventional PID control strategy, for example. Such a control strategy is implemented in a feedback controller 135, and for simplicity it is represented by the feedback loop 132. Of course, the feedback loop 132 may provide the measured actual pressure directly to the third proportional valve 130, as well.

The set point of the first pressure $P_1$ is calculated as a function of the second pressure $P_2$, measured at the pressure sensing port 162 by the second pressure sensor 123, the flow resistance R of the resistance portion 168, and a desired mass flow rate through the resistance portion 168. In the depicted embodiment, the set point of the first pressure $P_1$ is determined by the feedback controller 135, as discussed above. The feedback controller 135 receives pressure sensing feedback from the second pressure sensor 123 via an auxiliary feedback loop 131, indicating the value of the second pressure $P_2$. The flow resistance R may be previously stored in the feedback controller 135 or other processor in GC 100 that communicates with the feedback controller 135. The feedback controller 135 performs real-time calculations of the set point for the first pressure $P_1$ and controls it to the set point with the mechanism as represented by the feedback loop 132, as discussed above.

A representative relationship among the first pressure $P_1$, the second pressure $P_2$ and the flow resistance R is provided by Equation (1):

$$P_1^2 = P_2^2 + 1.4R \qquad (1)$$

In other words, the set point of the first pressure $P_1$ is the square root of the sum of the square of the second pressure $P_2$ and the flow resistance R of the flow resistance element 160. Because the flow resistance R is a known constant at a constant temperature (e.g., when the flow resistance element 160 is thermally controlled at the constant temperature $T_1$), the set point of $P_1$ may be determined and/or adjusted dynamically throughout chromatography operations by simply monitoring and accounting for changes in the measured value of the second pressure $P_2$, which reflects the resistance of the downstream column system 170. Meanwhile, the second mass flow rate (e.g., 0.1 ml/min) is provided by the second mass flow controller 120 to the pressure sensing port 162 of the flow resistance element 160. Thus, in order to supply the constant downstream mass flow rate (e.g., 1.5 ml/min) to downstream column system 170, the flow rate control system 105 only needs to control the additional constant flow resistance mass flow rate (e.g., 1.4 ml/min) from the pressure control port 161 to the flow resistance element 160, which is achieved by measuring the second pressure $P_2$ and controlling the first pressure $P_1$ to its required set point, as discussed above.

In this manner, the first pressure $P_1$ follows the set point of the first pressure $P_1$ dynamically throughout operation of the GC system 100 in order to maintain the constant downstream mass flow (e.g., 1.5 ml/min) to the downstream column system 170 via the flow resistance element 160. Therefore, as discussed above, the constant downstream mass flow is maintained without having to know the various characteristics of the downstream column system 170, such as the geometry, dimensions, number of thermal zones, temperature programs and the like.

Of course, the relationship among the first pressure $P_1$, the second pressure $P_2$, the flow resistance R, and the flow resistance mass flow rate may vary to provide unique benefits for any particular situation or to meet application specific design requirements of various implementations, as would be apparent to one having ordinary skill in the art. More generally, the relationship may be experimentally obtained, theoretically determined and/or empirically formulated using various fitting parameters. The relationship may be stored in a computer memory or within the feedback controller 135 as discussed above, for example. The downstream mass flow through the downstream column system 170 is therefore constant, regardless of the geometry, dimension, temperature programs and the like, with respect to the flow path downstream of the flow resistance element 160.

In various embodiments, the feedback controller 135, discussed above, may be configured separately to execute one or more logical or mathematical algorithms, including determination set points for the first pressure $P_1$, e.g., in accordance with Equation (1), above. The feedback controller 135 may be implemented by a processor, application specific integrated circuits (ASICs), field-programmable gate arrays (FPGAs), or combinations thereof, using software, firmware, hard-wired logic circuits, or combinations thereof. When using a processor, a memory (e.g., nonvolatile memory) (not shown) is included for storing executable software/firmware executable code that allows it to perform the various functions.

The memory may be any number, type and combination of nonvolatile read only memory (ROM) and volatile random access memory (RAM), and may store various types of information, such as signals and/or computer programs and software algorithms executable by the processor (and/or other components). The memory may include any number, type and combination of tangible computer readable storage media, such as a disk drive, an electrically programmable read-only memory (EPROM), an electrically erasable and programmable read only memory (EEPROM), a universal serial bus (USB) drive, and the like.

Figure 2:
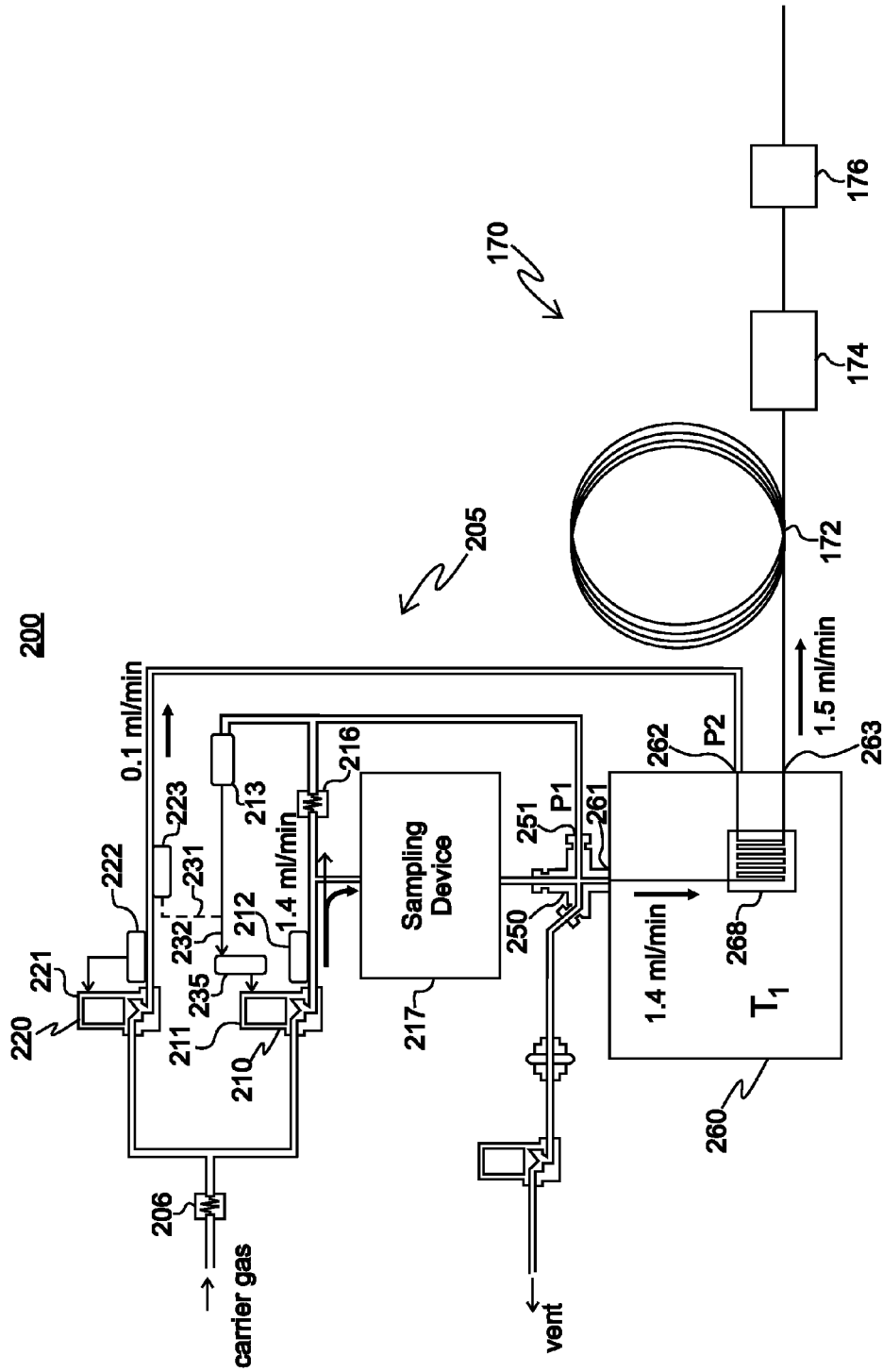
FIG. 2 is a block diagram illustrating a gas chromatography system including a constant mass flow rate control system, according to a representative embodiment.

FIG. 2 is a block diagram illustrating a gas chromatography system including a constant mass flow rate control system, according to another representative embodiment.

Referring to FIG. 2, GC system 200 has a gas sampling and inlet configuration that is operated in splitless injection mode, in which a split vent line is closed at inlet 250. The GC system 200 includes flow rate control system 205 and downstream column system 170. The downstream column system 170 is discussed above with reference to FIG. 1, and therefore the description will not be repeated.

The flow rate control system 205 has a first mass flow controller 210, which includes first proportional valve 211 and corresponding first flow sensor 212 for providing mass flow rate feedback. In an embodiment, the first mass flow controller 210 is a common or large full scale mass flow controller, as discussed above. The first mass flow controller 210 receives carrier gas from a carrier gas source (not shown), through optional flow resistant element 206, and controls the mass flow of the carrier gas to a predetermined first mass flow rate. In the depicted example, the first mass flow rate (as well as the flow resistance mass flow rate) is 1.4 ml/min for purposes of discussion, although other first mass flow rates may be incorporated in various implementations.

In the depicted embodiment, the first proportional valve 211 does not receive feedback from the first flow sensor 212. More specifically, control of the first pressure $P_1$ at the forward or downstream side of the first proportional valve 211 is achieved by constantly measuring the actual pressure at the inlet 250 with the pressure sensor 213 against a set point, and regulating gas out of the first proportional valve 211, according to a control strategy, such as conventional PID control strategy. Such a control strategy is implemented in a feedback controller 235, and for simplicity it is represented by the feedback loop 232. Of course, the feedback loop 232 may provide the measured actual pressure directly to the first proportional valve 221, as well. The mass flow rate of the carrier gas through first mass flow controller 210 is a predetermined first mass flow rate, which corresponds to a set point of the first pressure $P_1$ at inlet 250, as discussed below.

The carrier gas output by the first mass flow controller 210 is divided into first and second portions. The first portion of the carrier gas passes through a gas sampling device 217, as discussed above with respect to the gas sampling device 117, which provides a sample/carrier gas mixture to multi-port inlet 250. In an embodiment, the inlet 250 is substantially the same as the inlet 150 discussed above with reference to FIG. 1, except that the inlet 250 is configured so that it does not split the sample/carrier gas mixture (e.g., the split vent line is closed). The second portion of the carrier gas passes through flow resistant element 216 to pressure port 251 of the inlet 250, where a first pressure $P_1$ at the inlet 250 is measured by first pressure sensor 213.

The flow rate control system 205 also has a second mass flow controller 220, which includes second proportional valve 221 and corresponding second flow sensor 222 for providing mass flow rate feedback. In an embodiment, the second mass flow controller 220 may be a small full scale mass flow controller, for example, as discussed above with respect to second mass flow controller 120. The second mass flow controller 220 controls the mass flow rate of the carrier gas to a predetermined second mass flow rate. In the depicted example, the second mass flow rate is 0.1 ml/min for purposes of discussion, although other second mass flow rates may be incorporated in various implementations.

The flow rate control system 205 also includes a flow resistance element 260, which may be substantially the same as the flow resistance element 160, discussed above with reference to FIG. 1. The flow resistance element 260 has at least three ports, including inlet or pressure control port 261 connected to the inlet 250, pressure sensing port 262 connected to the second mass flow controller 220 and a second pressure sensor 223, and outlet port 263 connected to the downstream column system 170. A second pressure $P_2$ of the carrier gas at the pressure sensing port 262 is measured by the second pressure sensor 223. The flow resistance element 260 further includes resistance portion 268, which provides a finite flow resistance R between the pressure control port 261 and the pressure sensing port 262, similarly as discussed above with respect to the resistance portion 168 in FIG. 1.

The flow resistance element 260 outputs a constant downstream mass flow rate from the outlet port 263, which is the sum of the flow resistance mass flow rate through the resistance portion 268 and the second mass flow rate from the second mass flow controller 220. Thus, in the depicted example, the downstream mass flow rate is 1.5 ml/min, based on the illustrative flow resistance mass flow rate of 1.4 ml/min and second mass flow rate of 0.1 ml/min.

As described in U.S. Pat. No. 5,431,712, for example, the inlet 250 performs the splitless injection mode via a so-called forward pressure control scheme, implemented by the first proportional valve 211, the pressure sensor 213 and a feedback loop 232. More specifically, control of the first pressure $P_1$ at downstream side of the first proportional valve 211 is achieved by constantly measuring the actual pressure at the inlet 250 using the pressure sensor 213 against a set point and regulating gas out of the first proportional valve 211, according to a control strategy, such as conventional PID control strategy, for example. Such a control strategy is implemented in a feedback controller 235, and for simplicity it is represented by the feedback loop 232.

The set point of the first pressure $P_1$ is calculated as a function of the second pressure $P_2$, measured at the pressure sensing port 262 by the second pressure sensor 223, the flow resistance R of the resistance portion 268, and a desired mass flow rate through the flow resistance portion 268. In the depicted embodiment, the set point of the first pressure $P_1$ is determined by a feedback controller 235, for example. The feedback controller 235 receives pressure sensing feedback from the second pressure sensor 223 via an auxiliary feedback loop 231, indicating the value of the second pressure $P_2$. The flow resistance R may be previously stored in the feedback controller or other processor in GC 200 that communicates with the feedback controller 235. The feedback controller performs real-time calculations of the set point for the first pressure $P_1$ and controls it to the set point with the mechanism as represented by the feedback loop 232, as discussed above.

The feedback controller 235 determines the set point as a function of the second pressure $P_2$ from the second pressure sensor 223 and the flow resistance R of the resistance portion 268 of the flow resistance element 260. A representative relationship among the first pressure $P_1$, the second pressure $P_2$ and the flow resistance R is provided by Equation (1), above. Because the flow resistance R is a known constant, the set point of $P_1$ may be determined and/or adjusted dynamically throughout chromatography operations by simply monitoring and accounting for changes in the measured value of the second pressure $P_2$. Also, the flow rate control system 205 only needs to control an additional constant 1.4 ml/min flow from the pressure control port 261 to the flow resistance element 260, which is achieved by measuring the second pressure $P_2$ and controlling the first pressure $P_1$ to its required set point, as discussed above.

Of course, the relationship among the first pressure $P_1$, the second pressure $P_2$, the flow resistance R, and the flow resistance mass flow rate may vary to provide unique benefits for any particular situation or to meet application specific design requirements of various implementations, as would be apparent to one having ordinary skill in the art. Also, the feedback controller 235 may be implemented by a processor, ASICs, FPGAs, or combinations thereof, using software, firmware, hard-wired logic circuits, or combinations thereof, along with various memories, as discussed above with respect to the feedback controller 135 discussed above with reference to FIG. 1, and therefore corresponding descriptions will not be repeated.

In this manner, the first pressure $P_1$ follows the set point of the first pressure $P_1$ dynamically in order to maintain the constant downstream mass flow (e.g., 1.5 ml/min) to the downstream column system 170 from the flow resistance element 260. Therefore, as discussed above, the constant downstream mass flow is maintained without having to know the various characteristics of the downstream column system 170, such as the geometry, dimensions, number of thermal zones and/or temperature programs.

Figure 3:
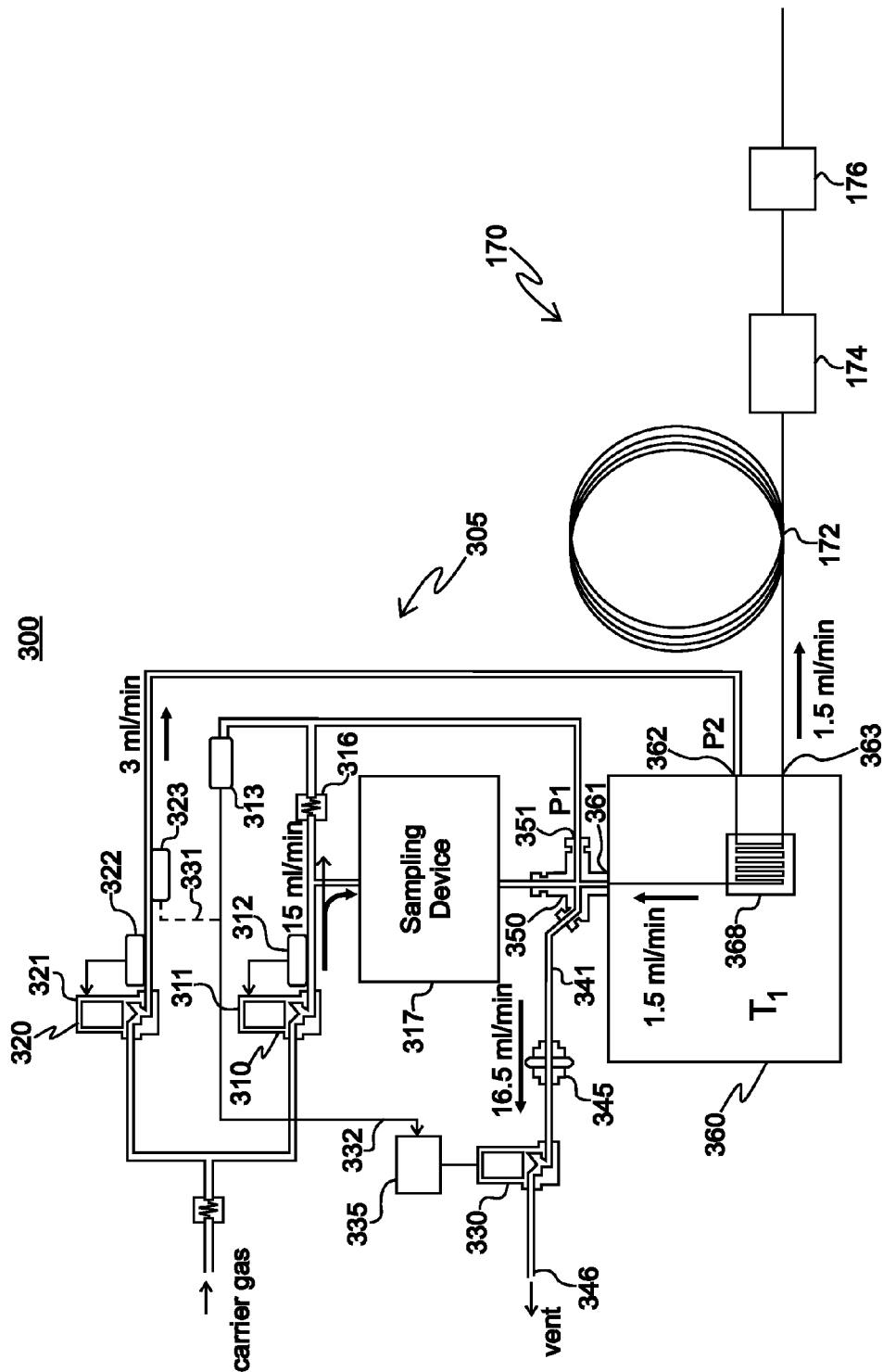
FIG. 3 is a block diagram illustrating a gas chromatography system including a constant mass flow rate control system, according to a representative embodiment.

FIG. 3 is a block diagram illustrating a gas chromatography system including a constant mass flow rate control system, according to another representative embodiment.

Referring to FIG. 3, GC system 300 has a backflush configuration, enabling a backflush operation, usually after sample injection is completed. The GC system 300 includes flow rate control system 305 and downstream column system 170. The downstream column system 170 is discussed above with reference to FIG. 1, and therefore the description will not be repeated.

The flow rate control system 305 has a first mass flow controller 310, which includes first proportional valve 311 and corresponding first flow sensor 312 for providing mass flow rate feedback. In an embodiment, the first mass flow controller 310 may be a common or large full scale mass flow controller, for example, and receives carrier gas from a carrier gas source (not shown), through optional flow resistant element 306. The first mass flow controller 310 controls the mass flow of the carrier gas to a predetermined first mass flow rate. In the depicted example, the first mass flow rate is 15 ml/min for purposes of discussion, although other first mass flow rates may be incorporated in various implementations.

The carrier gas output by the first mass flow controller 310 is divided into first and second portions, where the first portion dominates the second portion. The first portion of the carrier gas passes through a gas sampling device 317, as discussed above with respect to the gas sampling device 317, which injects sample into a sample inlet, depicted as representative multi-port inlet 350, e.g., a Volatiles Interface (VI).

The inlet 350 splits the sample/carrier gas mixture between split vent line 341 and the downstream column system 170 (via flow resistance element 360, discussed below). The second portion of the carrier gas passes through a flow resistant element 316 to pressure port 351 of the inlet 350, where a first pressure $P_1$ at the inlet 350 is measured by first pressure sensor 313.

The flow rate control system 305 also has a second mass flow controller 320, which includes second proportional valve 321 and corresponding second flow sensor 322 for providing flow rate feedback. In an embodiment, the second mass flow controller 320 may be a small full scale mass flow controller, for example, as discussed above with respect to second mass flow controller 120. The second mass flow controller 320 receives carrier gas from the carrier gas source (not shown) through the optional flow resistant element 306. The second mass flow controller 320 controls the mass flow of the carrier gas to a predetermined second mass flow rate. In the depicted example, the second mass flow rate is 3 ml/min for purposes of discussion, although other second mass flow rates may be incorporated in various implementations.

In addition, the flow rate control system 305 includes flow resistance element 360, which may be implemented by a pre-column chip, for example. As discussed above with respect to the flow resistance element 160, the flow resistance element 360 has at least three ports, including inlet or pressure control port 361 connected to the inlet 350, pressure sensing port 362 connected to the second mass flow controller 320 and a second pressure sensor 323, and outlet port 363 connected to the downstream column system 170. A second pressure $P_2$ of the carrier gas at the pressure sensing port 362 is measured by the second pressure sensor 323.

The flow resistance element 360 further includes resistance portion 368, which provides a finite backflush flow resistance R between the pressure sensing port 362 and the pressure control port 361. The resistance portion 368 may be a segment of capillary column, or a flow path fabricated in a closed substrate, such as a silicon chip or a metal plate, for example, as discussed above with respect to the resistance proton 168 of FIG. 1. The backflush flow resistance R has a known (e.g., previously determined) relationship for relating the backflush flow rate through the flow resistance element 360 with the pressure differential between the pressure sensing port 362 and the pressure control port 361, at a constant temperature $T_1$ (or in accordance with a temperature program), based on the type of carrier gas. In various embodiments, the backflush flow resistance R has a constant or fixed value at the temperature $T_1$. The value of the backflush flow resistance R may be determined and calibrated prior to operation, and the relationship may be theoretically derived, empirically characterized or experimentally calibrated, for example, without departing from the scope of the present teachings.

As stated above, GC system 300 has a backflush configuration, so the flow resistance mass flow rate (and thus corresponding fixed flow resistance) of the flow resistance element 360 is directed toward the inlet 350, and is referred to as the backflush mass flow rate. The backflush mass flow rate is 1.5 ml/min for purposes of discussion, although other backflush mass flow rates and corresponding flow resistances may be incorporated in various implementations, as would be apparent to one having ordinary skill in the art. Therefore, when the second mass flow controller 320 supplies the second mass flow rate of 3 ml/min to the pressure sensing port 362 of the flow resistance element 360, a 1.5 ml/min constant downstream mass flow is directed to the downstream column system 170, and the remaining 1.5 ml/min backflushes the flow resistance element 360 at the backflush mass flow rate of 1.5 ml/min. In other words, the flow resistance element 360 outputs a constant downstream mass flow rate from the outlet port 363, which is the second mass flow rate from the second mass flow controller 320 less the backflush mass flow rate through the resistance portion 368.

In an embodiment, the split vent line 341 includes third proportional valve 330, optional vent trap 345 and vent 346. In an embodiment, the inlet 350 is substantially the same as the inlet 150 discussed above with reference to FIG. 1, except that the inlet 350 is configured so that it receives the backflush mass flow rate from the flow resistance element 360, as well as the first mass flow from the first mass flow controller 310 via the gas sampling device 317. In the depicted example, the vented mass flow rate is 16.5 ml/min for purposes of discussion, which is the sum of the first mass flow rate (e.g., 15 ml/min) and the backflush mass flow rate (e.g., 1.5 ml/min), although other first mass flow rates and backflush mass flow rates may be incorporated in various implementations.

As described in U.S. Pat. No. 5,431,712, for example, the inlet 350 performs so-called backpressure control scheme, implemented by the third proportional valve 330, the pressure sensor 313 and a feedback loop 332. More specifically, control of the first pressure $P_1$ at the back or upstream side of the third proportional valve 330 is achieved by constantly measuring the actual pressure at the inlet 350 using the pressure sensor 313 against a set point and regulating gas out of the third proportional valve 330, according to a control strategy, such as conventional PID control strategy, for example. Such a control strategy is implemented in a feedback controller 335, and for simplicity it is represented by the feedback loop 332.

The set point of the first pressure $P_1$ is calculated as a function of the second pressure $P_2$, measured at the pressure sensing port 362 by the second pressure sensor 323, the backflush flow resistance R of the resistance portion 368, and a desired mass flow rate through the flow resistance portion 368. In the depicted embodiment, the set point of the first pressure $P_1$ is determined by the feedback controller 335, for example. The feedback controller 335 receives pressure sensing feedback from the second pressure sensor 323 via an auxiliary feedback loop 331, indicating the value of the second pressure $P_2$. The backflush flow resistance R may be previously stored in the feedback controller or other processor in GC 300 that communicates with the feedback controller. The feedback controller 335 performs real-time calculations of the set point for the first pressure $P_1$ and controls it to the set point with the mechanism as represented by the feedback loop 332, as discussed above.

A representative relationship among the first pressure $P_1$, the second pressure $P_2$ and the backflush flow resistance R is provided by Equation (2):

$$P_1^2 = P_2^2 - 1.5R \qquad (2)$$

In other words, the set point of the first pressure $P_1$ is the square root of the difference between the square of the second pressure $P_2$ and the backflush flow resistance R of the flow resistance element 360. Because the backflush flow resistance R is a known constant (e.g., when the flow resistance element 360 is thermally controlled at the constant temperature $T_1$), the set point of $P_1$ may be determined and/or adjusted dynamically throughout chromatography operations by simply monitoring and accounting for changes in the measured value of the second pressure $P_2$. Meanwhile, the second mass flow rate (e.g., 3 ml/min) is provided by the second mass flow controller 320 to the pressure sensing port 362 of the flow resistance element 360. Thus, in order to supply the constant downstream mass flow rate (e.g., 1.5 ml/min) to downstream column system 170, the flow rate control system 305 only needs to control the additional backflush flow resistance mass flow rate (e.g., 1.5 ml/min) to the pressure control port 361, which is achieved by measuring the second pressure $P_2$ and controlling the first pressure $P_1$ to its required set point, as discussed above.

In this manner, the first pressure $P_1$ follows the set point of the first pressure $P_1$ dynamically throughout operation of the GC system 300 in order to maintain the constant downstream mass flow (e.g., 1.5 ml/min) to the downstream column system 170 via the flow resistance element 360. Therefore, as discussed above, the constant downstream mass flow is maintained without having to know the various characteristics of the downstream column system 170, such as the geometry, dimensions, number of thermal zones and/or temperature programs.

Of course, the relationship among the first pressure $P_1$, the second pressure $P_2$, the backflush flow resistance R, and the backflush flow resistance mass flow rate may vary to provide unique benefits for any particular situation or to meet application specific design requirements of various implementations, as would be apparent to one having ordinary skill in the art. Also, the feedback controller 335 may be implemented by a processor, ASICs, FPGAs, or combinations thereof, using software, firmware, hard-wired logic circuits, or combinations thereof, along with various memories, as discussed above with respect to the feedback controller discussed above with reference to FIG. 1, and therefore the corresponding descriptions will not be repeated.

Throughout the specification, the various gas flow rates and flow resistances are illustrative. It is understood that the gas flow rates and flow resistances may vary to provide unique benefits for any particular situation or to meet application specific design requirements of various implementations, as would be apparent to one having ordinary skill in the art.

While specific embodiments are disclosed herein, many variations are possible, which remain within the concept and scope of the invention. Such variations would become clear after inspection of the specification, drawings and claims herein. The invention therefore is not to be restricted except within the scope of the appended claims.

What is claimed is:

1. A device for providing a constant mass flow rate to a downstream column system of a gas chromatograph, the device comprising:

a small full scale mass flow controller configured to control a carrier gas to flow at a first mass flow rate;

a flow resistance element having a finite flow resistance, the flow resistance element comprising an inlet port connected to a sample inlet, an outlet port connected to the downstream column system, and a pressure sensing port in fluid communication with both the outlet port and the small full scale mass flow controller for receiving the carrier gas at the first mass flow rate;

a sample inlet pressure controller configured to control the sample inlet at a first pressure; and a pressure sensor configured to measure a second pressure of the carrier gas at the pressure sensing port of the flow resistance element, wherein a set point of the first pressure is determined as a function of the second pressure, the flow resistance of the flow resistance element, and a second mass flow rate from the inlet port to the outlet port of the flow resistance element, and the mass flow rate to the downstream column system is kept constant by controlling the first pressure to equal the first pressure set point.

2. The device of claim 1, wherein the mass flow rate to the downstream column system is a sum of the first mass flow rate and the second mass flow rate.

3. The device of claim 2, wherein the second mass flow rate of the flow resistance element is controlled in response to the first pressure at the sample inlet.

4. The device of claim 1, wherein the sample inlet pressure controller comprises:
   a large full scale mass flow controller configured to control the carrier gas to flow at a third mass flow rate; and
   a second pressure sensor measuring the first pressure of the third mass flow rate carrier gas.

5. The device of claim 4, wherein the sample inlet is configured for split injection, the sample inlet splitting the third mass flow rate carrier gas between the flow resistance element and a split vent line.

6. The device of claim 5, wherein the sample inlet pressure controller further comprises:
   a proportional valve in the split vent line configured to adjust the first pressure at the sample inlet.

7. The device of claim 6, wherein the proportional valve adjusts the first pressure by controlling a flow resistance through the proportional valve.

8. The device of claim 4, wherein the sample inlet is configured for splitless injection.

9. The device of claim 8, wherein the large full scale mass flow controller comprises a corresponding proportional valve configured to adjust the first pressure at the sample inlet.

10. The device of claim 4, wherein the sample inlet is configured for split injection and backflush, the sample inlet directing backflushed carrier gas from the flow resistance element to a split vent line.

11. The device of claim 10, further comprising:
    a proportional valve in the split vent line configured to adjust the first pressure at sample inlet based on the first pressure.

12. The device of claim 11, wherein the proportional valve adjusts the first pressure by controlling a flow resistance through the proportional valve.

13. The device of claim 1, further comprising:
    a feedback controller connected to the pressure sensor and configured to determine the set point of the first pressure.

14. The device of claim 13, wherein the set point is the square root of the sum of the measurement of the second pressure and the flow resistance of the flow resistance element.

15. The device of claim 13, wherein the set point is the square root of the difference between the measurement of the second pressure and a backflush flow resistance of the flow resistance element.

16. A device for providing a constant mass flow rate to a downstream column system of a gas chromatograph, the device comprising:
    a mass flow controller configured to output carrier gas at a first mass flow rate;
    a flow resistance element having a finite flow resistance, the flow resistance element comprising an inlet port connected to a sample inlet, an outlet port connected to the downstream column system, and a pressure sensing port in fluid communication with the outlet port and an output side of the mass flow controller;
    sample inlet pressure control means configured to control the sample inlet at a first pressure;
    a pressure sensor configured to measure a second pressure at the pressure sensing port of the flow resistance element; and
    a feedback controller configured to determine a set point of the first pressure, the set point being a value of the first pressure that produces a second mass flow rate through the flow resistance element,
    wherein the feedback controller determines the set point of the first pressure based on measurements of the second pressure from the pressure sensor in order to keep the downstream flow rate input to the downstream column at a constant value.

17. A method for providing a constant mass flow rate from a flow resistance element to a downstream column system of a gas chromatograph, the flow resistance element comprising an inlet port connected to a sample inlet, an outlet port connected to the downstream column system, and a pressure sensing port in fluid communication with the outlet port and a small full scale mass flow controller for receiving the carrier gas from the small full scale mass flow controller, the method comprising:
    controlling the carrier gas at the small full scale mass flow controller to flow at a first mass flow rate;
    controlling the sample inlet at a first pressure;
    measuring a second pressure of the carrier gas at the pressure sensing port of the flow resistance element at a pressure sensor;
    determining a set point of the first pressure as a function of the second pressure, a finite flow resistance of the flow resistance element, and a second mass flow rate from the inlet port to the outlet port of the flow resistance element; and
    controlling the first pressure to match the determined set point to keep the mass flow rate to the downstream column system constant.

18. The method of claim 17, wherein the mass flow rate to the downstream column system is a sum of the first mass flow rate and the second mass flow rate.

19. The device of claim 17, wherein determining the set point comprises calculating the square root of the sum of the measurement of the second pressure and the flow resistance of the flow resistance element.

20. The device of claim 17, wherein determining the set point comprises calculating the square root of the difference between the measurement of the second pressure and a backflush flow resistance of the flow resistance element.

* * * * *

UNITED STATES PATENT AND TRADEMARK OFFICE
CERTIFICATE OF CORRECTION

PATENT NO. : 8,343,258 B2  
APPLICATION NO. : 12/749682  
DATED : January 1, 2013  
INVENTOR(S) : Xiaosheng Guan Page 1 of 1

It is certified that error appears in the above-identified patent and that said Letters Patent is hereby corrected as shown below:

In the Claims:

In column 14, line 47, in claim 19, delete "device" and insert -- method --, therefor.

In column 14, line 51, in claim 20, delete "device" and insert -- method --, therefor.

Signed and Sealed this  
Sixteenth Day of April, 2013

Teresa Stanek Rea  
*Acting Director of the United States Patent and Trademark Office*